United States Patent
Sakakura et al.

(10) Patent No.: US 7,067,696 B2
(45) Date of Patent: Jun. 27, 2006

(54) PROCESS FOR PRODUCING (METH)ACROLEIN OR (METH)ACRYLIC ACID

(75) Inventors: Yasuyuki Sakakura, Tokyo (JP);
Shuhei Yada, Yokkaichi (JP);
Hirochika Hosaka, Yokkaichi (JP);
Yasushi Ogawa, Yokkaichi (JP);
Yoshiro Suzuki, Yokkaichi (JP)

(73) Assignee: Mitsubishi Chemical Corporation, Tokyo (JP)

( * ) Notice: Subject to any disclaimer, the term of this patent is extended or adjusted under 35 U.S.C. 154(b) by 0 days.

(21) Appl. No.: 10/863,511

(22) Filed: Jun. 9, 2004

(65) Prior Publication Data

US 2005/0038290 A1    Feb. 17, 2005

Related U.S. Application Data

(63) Continuation of application No. PCT/JP02/12912, filed on Dec. 10, 2002.

(30) Foreign Application Priority Data

Dec. 13, 2001    (JP) .............................. 2001-379526

(51) Int. Cl.
*C07C 51/16* (2006.01)
*C07C 45/35* (2006.01)
(52) U.S. Cl. ...................................... 562/547; 568/479
(58) Field of Classification Search ............... None
See application file for complete search history.

(56) References Cited

U.S. PATENT DOCUMENTS

| 4,031,135 A | 6/1977 | Engelbach et al. |
| 4,147,885 A | 4/1979 | Shimizu et al. |
| 4,365,087 A | 12/1982 | Kadowaki et al. |
| 2001/0003783 A1* | 6/2001 | Nishimura et al. ......... 562/512 |

FOREIGN PATENT DOCUMENTS

| EP | 0 990 636 A1 | 4/2000 |
| JP | 53-15314 A | 2/1978 |

* cited by examiner

*Primary Examiner*—Paul A. Zucker
(74) *Attorney, Agent, or Firm*—Nixon & Vanderhye P.C.

(57) ABSTRACT

In the process for producing (meth)acrolein or (meth)acrylic acid, which comprises feeding a raw material of the (meth) acrolein or (meth)acrylic acid, and a molecular oxygen-containing gas mixed with a diluting gas and compressed by a compressor, to an oxidation reactor to conduct a catalytic gas-phase oxidation reaction therebetween; feeding the obtained reaction gas to an absorption column to contact with water; recovering an aqueous solution of the (meth) acrolein or (meth)acrylic acid from a bottom of the absorption column and an exhaust gas from a top of the absorption column; and recycling a part or whole of the thus recovered exhaust gas to use as the diluting gas, the temperature of the mixed gas at a suction inlet of the compressor is controlled to a temperature higher than a dew point thereof. According to the process of the present invention, the compressor is prevented from suffering from clogging or damage thereto.

7 Claims, 1 Drawing Sheet

PROCESS FOR PRODUCING (METH)ACROLEIN OR (METH)ACRYLIC ACID

This application is a continuation of PCT International Application No. PCT/JP02/12912, filed in Japanese on 10 Dec. 2002, which designated the US. PCT/JP02/12912 claims priority to JP Application No. 2001-379526 filed 13 Dec. 2001. The entire contents of these applications are incorporated herein by reference.

TECHNICAL FIELD

The present invention relates to a process for producing (meth)acrolein or (meth)acrylic acid.

BACKGROUND ARTS

There is known the process for producing (meth)acrolein or (meth)acrylic acid, which comprises the steps of feeding a raw material of the (meth)acrolein or (meth)acrylic acid, and a molecular oxygen-containing gas mixed with a diluting gas and compressed by a compressor, to a oxidation reactor to conduct a catalytic gas-phase oxidation reaction therebetween; feeding the obtained reaction gas to an absorption column to contact with water; recovering an aqueous solution of the (meth)acrolein or (meth)acrylic acid from a bottom of the absorption column and an exhaust gas from a top of the absorption column; and recycling a part or whole of the thus recovered exhaust gas to reuse as the diluting gas (for example, Japanese Patent Application Laid-open (KOKAI) No. 2001-220362).

In the above conventional process, the diluting gas has been used to prevent the composition of raw gas obtained by mixing the raw material of (meth)acrolein or (meth)acrylic acid with the molecular oxygen-containing gas from falling within a range of explosion thereof.

The exhaust gas recovered from a top of the absorption column contains aldehydes, acetic acid, terephthalic acid as a sublimatable substance, etc., which are by-produced by the catalytic gas-phase oxidation reaction, as well as a considerable amount of the (meth)acrolein or (meth)acrylic acid and water. Therefore, low-boiling components such as aldehydes contained in the exhaust gas tend to be condensed and solidified by polycondensation reaction thereof. The thus produced solids tend to be deposited in conduits of the reactor, finally resulting in clogging thereof.

To solve these problems, the above Japanese Patent Application (KOKAI) has proposed the method of heating the exhaust gas used as the diluting gas to a temperature not less than the same temperature as that of a top gas of the absorption column.

The above method can be effective to prevent clogging in conduits, etc., disposed on an upstream side of the position where the exhaust gas and the molecular oxygen-containing gas are mixed with each other. However, since the molecular oxygen-containing gas is usually used in a relatively large amount as compared to the exhaust gas, the temperature of the exhaust gas decreases subsequent to mixing with the molecular oxygen-containing gas, thereby failing to sufficiently prevent the conduits, etc., from clogging. In particular, the compressor tends to suffer from problems such as clogging or damage.

Accordingly, an object of the present invention is to provide a process for producing (meth)acrolein or (meth) acrylic acid, which comprises the steps of feeding a raw material of the (meth)acrolein or (meth)acrylic acid, and a molecular oxygen-containing gas mixed with a diluting gas and compressed by a compressor, to a oxidation reactor to conduct a catalytic gas-phase oxidation reaction therebetween; feeding the obtained reaction gas to an absorption column to contact with water; recovering an aqueous solution of the (meth)acrolein or (meth)acrylic acid from a bottom of the absorption column and an exhaust gas from a top of the absorption column; and recycling a part or whole of the thus recovered exhaust gas to use as the diluting gas, which process is capable of preventing the compressor from suffering from clogging or damage.

DISCLOSURE OF THE INVENTION

Figure 1:
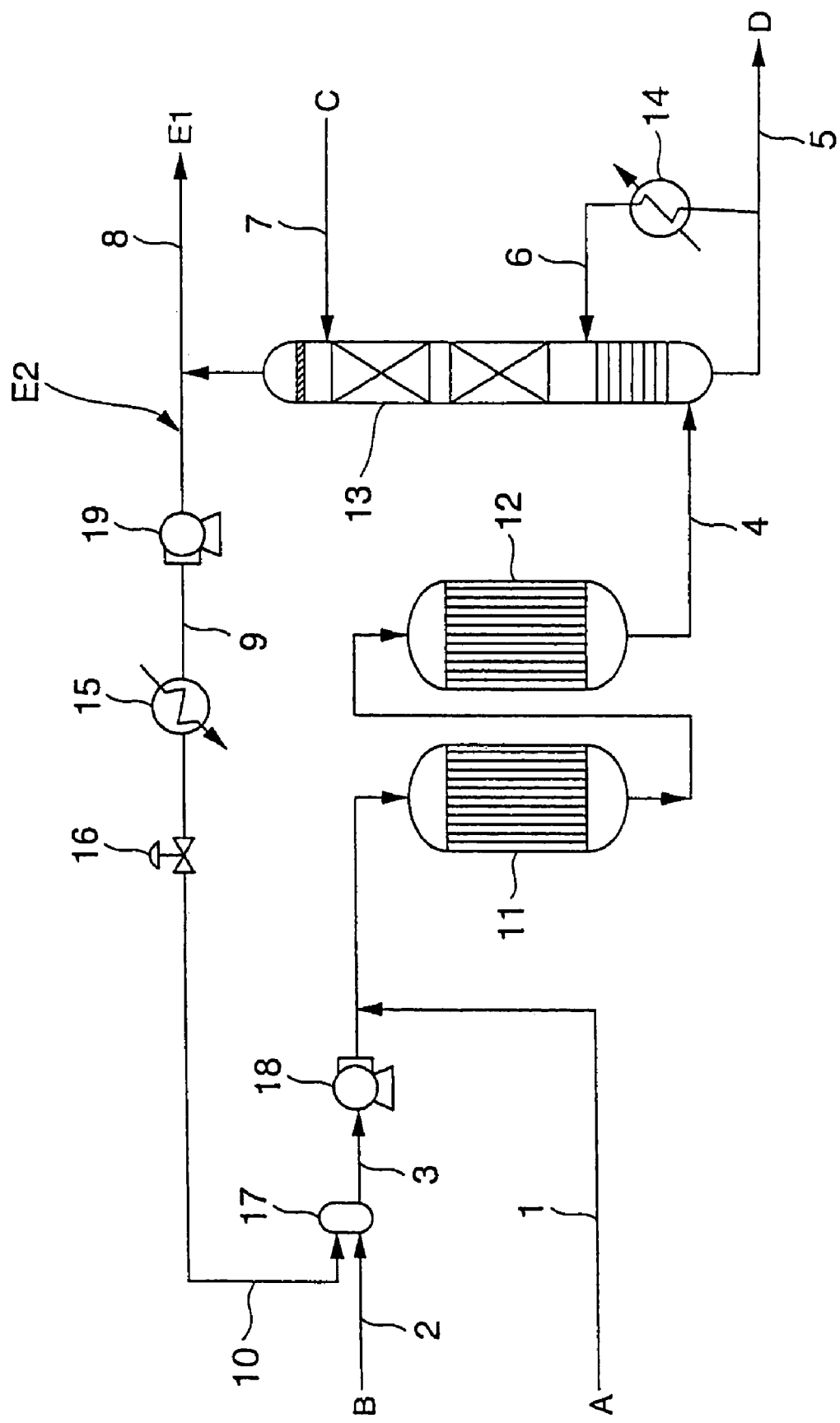
FIG. 1 is a flow sheet showing an example of the process according to the present invention.

As a result of the present inventors' earnest studies for solving the above problems, it has been found that by controlling the temperature of the mixed gas at a suction inlet of the compressor to a temperature higher than a dew point thereof, the mixed gas can be inhibited from suffering from formation of mists therein even in the case where a relatively large amount of the molecular oxygen-containing gas is mixed with the exhaust gas.

The present invention has been attained on the basis of the above finding. In an aspect of the present invention, there is provided a process for producing (meth)acrolein or (meth) acrylic acid, wherein in the above-mentioned process, the temperature of the mixed gas composed of the molecular oxygen-containing gas and the diluting gas at a suction inlet of the compressor is controlled to a temperature higher than a dew point thereof.

The process of the present invention is described in detail below with reference to the accompanying drawing.

First, in the process of the present invention, the catalytic gas-phase oxidation reaction is performed. That is, a raw material (A), and a molecular oxygen-containing gas (B) mixed with a diluting gas and compressed by a compressor (18) are fed to an oxidation reactor (11), (12).

As the raw material (A), there may be used the following compounds. Namely, there may be used propylene for production of acrolein, and isobutylene or t-butanol for production of methacrolein. Meanwhile, since (meth)acrolein is an intermediate for production of (meth)acrylic acid, the acrylic acid may be produced from raw propylene via acrolein, and methacrylic acid may be produced from raw isobutylene or t-butanol via methacrolein. Also, as the molecular oxygen-containing gas (B), there may be usually used air (the "molecular oxygen-containing gas" is hereinafter referred to merely as "air"). The details of the diluting gas will be described later.

The oxidation reactor includes a front-stage reactor (11) and a rear-stage reactor (12). As the respective reactors, there may be used a multipipe-type reactor equipped with a large number of reaction tubes filled with an oxidation catalyst. Also, there may be used an oxidation reactor of such a type in which the front-stage and rear-stage reactors are integrally combined. The front-stage and rear-stage reactors (11) and (12) are filled with different oxidation catalysts. The respective temperatures of the oxidation catalysts are controlled to an optimum reaction temperature by circulating a heating medium (not shown) on an outside of the reaction tubes.

The front-stage oxidation reactor (11) is filled with a catalyst for production of (meth)acrolein, and the rear-stage oxidation reactor (12) is filled with a catalyst for production of (meth)acrylic acid. As the former catalyst filled in the front-stage reactor, there may be used, for example, Mo—Bi-based composite oxide catalysts having a composition of Mo—Bi—Fe—Co—Ni—B—Na—Si—O, and as the latter catalyst filled in the rear-stage reactor, there may be used, for example, Mo—V-based composite oxide catalysts having a composition of Mo—V—Sb—Ni—Cu—Si—O. The heterogeneous catalyst gas-phase oxidation reaction may be conducted under known conditions suitable for the respective catalysts. Alternatively, acrylic acid may also be produced by such a gas-phase catalytic oxidation process using propane as a raw material as well as Mo—Bi—Te-based composite oxide catalysts, Mo—Bi—Sb-based composite oxide catalysts, etc.

In the present invention, the concentration of combustible gasses in the raw gas composed of the raw material, the diluting gas and air (B) may be controlled to the range of usually 5 to 8% by volume. More specifically, the composition of the raw gas is preferably controlled such that a volume percentage of air is 40 to 70% (of which 21% by volume is occupied by oxygen), a volume percentage of water is 5 to 12%, and a volume percentage of an inert gas such as nitrogen and carbon dioxide gas except for nitrogen contained in air mixed is 16 to 48%.

Meanwhile, in the flow sheet shown in FIG. 1, a whole amount of the reaction gas generated from the front-stage oxidation reactor (11) is fed to the rear-stage oxidation reactor (12) for producing (meth)acrylic acid. On the other hand, in the case where the reaction gas is directly fed from the front-stage oxidation reactor (11) to an absorption column (13) described in detail later, (meth)acrolein can be produced. Accordingly, for convenience, only the process for producing (meth)acrylic acid is explained below.

Next, in the process of the present invention, an aqueous solution of (meth)acrylic acid is recovered. More specifically, the reaction gas generated at the rear-stage oxidation reactor (12) is fed to the absorption column (13) to contact with water. As the absorption column (13), there may be used such a column having trays at a lower portion thereof and a mist separator at a top thereof as shown in FIG. 1.

In the present invention, the oxidation reaction gas may be cooled to a temperature of 120 to 170° C. by a condenser (not shown), and then fed to a lower portion of the absorption column (13) through a line (4) to contact with water (C) supplied to an upper portion of the absorption column (13) through a line (7). At this time, it is preferred that a part of a bottom liquid of the absorption column is removed therefrom, cooled by a heat exchanger (14) and then circulated to an intermediate portion of the absorption column (13) through a line (6).

An aqueous solution (D) of (meth)acrylic acid is recovered from the bottom of the absorption column through a line (5) and then fed to a (meth)acrylic acid purification step (not shown). Whereas, the exhaust gas is recovered from the top of the absorption column through a line (9) and then used as the above diluting gas.

As the water (C), there may be used a waste water recovered from the (meth)acrylic acid purification step. When the amount of water (C) required is higher than that of the waste water recovered from the purification step, pure water, condensed water obtained from steam, low-concentration waste water discharged from a vacuum system of the (meth)acrylic acid purification step, etc., may be further added to the waste water from the purification step.

The amount of water (C) fed to the absorption column (13) is usually 0.05 to 0.5 kg/m$^3$, preferably 0.1 to 0.2 kg/m$^3$ base on the amount of the exhaust gas recovered from the top of the absorption column. The temperature of water (C) is usually 30 to 80° C., preferably 35 to 45° C. When the temperature of water (C) is too high, the absorption efficiency for (meth)acrylic acid tends to be deteriorated, so that the amount of (meth)acrylic acid mixed in the exhaust gas tends to be increased, resulting in deteriorated yield of (meth)acrylic acid. The temperature at the top of the absorption column (13) is adjusted to a dew point of the exhaust gas depending upon amount and temperature of water (C) fed thereto.

When the temperature of the exhaust gas recovered from the top of the absorption column (13) exceeds the dew point, (meth)acrylic acid, etc., tend to be mixed in the exhaust gas similarly to the above case, resulting in deterioration in yield of the (meth)acrylic acid. The temperature of the exhaust gas is usually 40 to 80° C., and the concentration of water in the exhaust gas is usually 5 to 40% by volume. The temperature of the exhaust gas can be raised by not only increasing the amount of water (C) fed to the absorption column (13) through the line (7) but also raising the temperature of the circulated liquid by control of the heat exchanger (14).

The amount of the exhaust gas (E2) (i.e., the exhaust gas used as the diluting gas) recovered through the line (9) is usually not less than 20% by volume, preferably 20 to 60% by volume based on the whole exhaust gas generated. Meanwhile, in the present invention, the whole exhaust gas may be used as the diluting gas.

In the process of the present invention, the exhaust gas (E2) is heated by the heat exchanger (15) and fed through a flow control valve (16) to a line (10). Whereas, air (B) is fed to the line (2), and then mixed with the exhaust gas. The thus obtained mixed gas is fed to the compressor (18). Meanwhile, in the case where it is required to pressurize the exhaust gas (E2) for circulation thereof, a compressor (19) may be disposed. Also, a part of the gas (E1) discharged from the top of the absorption column (13) may be fed through a line (8) to any suitable purification device (not shown) for converting the top gas into a harmless gas, and then discharged into atmospheric air.

In the present invention, both the gases fed to the compressor (18) are preferably previously mixed with each other by the mixer (17). More specifically, when the high-temperature exhaust gas (E2) containing water is mixed with the low-temperature air (B), the high-temperature gas tends to be cooled at a boundary surface between both the gases, resulting in condensation of water contained therein. In order to minimize the region where such a condensation of water occurs, the mixer (17) is preferably used as a means for rapidly mixing the two kinds of gases.

Although the mixer is not particularly restricted, there are preferably used mixers having a less pressure loss. Examples of the mixer usable in the present invention may include in-line type mixers having conduits fitted with spiral-shaped, cross-shaped, grid-shaped or orifice plate, etc., tank-type mixers into which two kinds of gases can be introduced in different directions to form a turbulent flow therein, or which are provided therein with a dispersing device such as a sparger or a porous plate, venturi-type mixers, or the like.

As the diluting gas, there may be used the exhaust gas discharged from the top of the absorption column (13) and/or a gas obtained by subjecting the exhaust gas to combustion treatment, etc., to convert the gas into a harmless one. A whole amount of water required in the oxidation reaction may be supplied by water contained in the exhaust gas (E2). When the amount of water supplied from the exhaust gas (E2) is insufficient to cover the amount of water required for the oxidation reaction, steam may be added to the exhaust gas (E2) or to the mixed gas obtained after mixing air (B) with the exhaust gas (E2). The temperature of the steam added is preferably not less than 100° C.

On the other hand, the temperature of air (B) is usually 0 to 30° C. Therefore, the temperature of the mixed gas tends to be influenced by that of air (B) (outside air). When the exhaust gas (E2) is contacted with the low-temperature air, the temperature of the resultant mixed gas is decreased to not more than the dew point thereof, so that water contained therein tends to be condensed into fine water droplets. In particular, in the winter season, this problem tends to become more remarkable owing to lower temperature of the outside air. Meanwhile, the dew point of the mixed gas which may be calculated from water concentration and pressure thereof, is usually 30 to 55° C.

In the production process of the present invention, the temperature of the mixed gas at the suction inlet of the compressor (18) is raised to not less than the dew point thereof. Namely, the temperature of the mixed gas at the suction inlet of the compressor (18) is usually higher by 5 to 20° C. than the dew point thereof. More specifically, the temperature of the mixed gas at the suction inlet of the compressor is in the range of usually 35 to 70° C., preferably 40 to 60° C. When the temperature of the mixed gas at the suction inlet of the compressor is too high, the volume of the gas sucked into the compressor (18) tends to become large, resulting in increase in power consumption of the compressor (18) and, therefore, uneconomical procedure.

In the present invention, in order to raise the temperature of the mixed gas at the suction inlet of the compressor (18) to not less than the dew point, the diluting gas is preferably heated to a temperature of 40 to 160° C. when mixed with air (B) (outside air). For example, in the winter season in which the outside air temperature is lowered up to 0° C., the temperature of the exhaust gas (E2) is usually adjusted to 60 to 160° C., and when the outside air temperature is 30° C., the temperature of the exhaust gas (E2) is usually adjusted to 40 to 120° C.

In the present invention, the diluting gas is preferably heated before mixing with air (B). In addition, the heating of the exhaust gas (E2) may be performed using the heat exchanger (15) or a means for mixing with steam. The type of the heat exchanger (15) used herein is not particularly restricted, and there may be used those heat exchangers whose inside can be cleaned, since the exhaust gas (E2) tends to contain (meth)acrylic acid, low-molecular aldehydes, sublimatable substances, etc.

When the flow amount of air (B) is larger than that of the exhaust gas (E2) mixed therewith, the air may be previously heated before mixing. The temperature of air (B) upon mixing with the diluting gas is usually 30 to 70° C., preferably 30 to 55° C. When the temperature of air (B) is maintained in the above-specified range, the compressor (18) can be advantageously prevented from being adversely affected by change in temperature of atmospheric air. The heating of the exhaust gas (E2) may be used in combination with the heating of air (B).

Even though the two kinds of gases are rapidly mixed together using the mixer (17), it may be difficult to inhibit occurrence of partial water condensation which will be caused by partially cooling the high-temperature exhaust gas (E2) at a boundary surface therebetween, as well as formation of fine water droplets. However, it is considered that since the amount of fine water droplets is extremely small, the fine water droplets are evaporated until the mixed gas reaches and enters the compressor (18). In order to ensure such an evaporation of the water droplets, the residence time of the mixed gas from the mixing of the diluting gas with air (B) to the introduction of the mixed gas into the compressor (18), is preferably adjusted to 0.3 to 1.5 seconds.

When the residence time is less than 0.3 second, it is required to more rapidly mix these gases with each other, resulting in occurrence of large pressure loss in the mixer. As a result, the power required for operating the compressor (18) tends to be considerably increased. On the other hand, when the residence time exceeds 1.5 seconds, a length of the conduit extending from the mixing step to the compressor (18) is too large, so that the mixed gas flowing through the conduit tends to be cooled by outside air to a temperature lower than the dew point.

When the exhaust gas (E2) and the air (B) are mixed together on the suction side of the compressor (18), any pressure drop is not caused. However, when the mixer (17) is disposed on an upstream side of the compressor, the pressure loss caused at the mixer tends to occasionally produce a slight negative pressure on the suction side of the compressor (18). The slight negative pressure on the suction side of the compressor is preferred because this leads to the effect of reducing the dew point which is useful for preventing the condensation of water in the mixed gas. However, when the negative pressure produced on the suction side of the compressor is too large, the power required for operating the compressor (18) is considerably increased. The pressure of the mixed gas (3) at the suction inlet of the compressor (18) is preferably in the range of from atmospheric pressure to the pressure lower by 10% than the atmospheric pressure.

When the mixing volume ratio of the air to the exhaust gas (E2) in the mixer is adjusted to 0.7:1 to 3.6:1, the composition of the mixed gas at the suction inlet of the compressor (18) is preferably controlled such that the volume ratio (%) of air: water: inert gas is 40 to 76%:5 to 13%:10 to 50% (the volume of the inert gas excludes that of nitrogen gas contained in air mixed).

PREFERRED EMBODIMENT OF THE PRESENT INVENTION

The present invention is described in more detail by Examples, but the Examples are only illustrative and not intended to limit the scope of the present invention.

EXAMPLE 1

In the process for production of acrylic acid as shown in FIG. 1, exhaust gas (E2) was discharged from a top of absorption column (13) and fed through line (9) to finned tube-type heat exchanger (15) where the gas was heated to 115° C. The exhaust gas was then fed through flow control valve (16) and line (10) to in-line type mixer (17) provided therein with a spiral member. Simultaneously, air (B) maintained at 15° C. was fed through line (2) to the mixer and mixed therein with exhaust gas (E2). A mixing ratio of exhaust gas (E2) to air (B) was 0.61:1.

The temperature and pressure of the resultant mixed gas at a suction inlet of compressor (18) were 53° C. and 100 kPa, respectively, and a residence time of the mixed gas from mixer (17) to the suction inlet of compressor (18) was 0.5 second. Also, the measured dew point of the mixed gas at the suction inlet of compressor (18) was 43° C. Further, it was confirmed that the mixed gas had such a composition that a volume ratio (%) of air: water: inert gas was 61.3: 8.7:30.

After pressurizing the mixed gas by compressor (18), propylene was added thereto so as to obtain a raw gas having a composition composed of 7% by volume of propylene, 57% by volume of air, 8% by volume of water and 28% by volume of inert gas (excluding nitrogen gas contained in air mixed). 100 Nm$^3$ of the thus obtained raw gas was fed to front-stage oxidation reactor (11) and successively to rear-stage oxidation reactor (12).

The reaction gas having a temperature of 260° C. which was obtained from rear-stage oxidation reactor (12) was cooled to 170° C. by a heat exchanger and then fed through line (4) to absorption column (13) having an inner diameter of 200 mm which was provided at a lower portion thereof with five-stage trays and was filled with a 2 m-height layer composed of "CASCADE MINIRING 2P" produced by Dodwel Inc., at an upper portion thereof. A part of an aqueous acrylic acid solution removed from a bottom of the absorption column was cooled to 55° C. by heat exchanger (14) and circulated through line (6) to an intermediate portion of the absorption column to rapidly cool and condense the reaction gas. Aqueous solution (C) containing 200 ppm of hydroquinone was supplied from a top of absorption column (13) at a feed rate of 15.5 1/hr.

The exhaust gas (E2) had a composition composed of 0.04% by volume of acrylic acid, 20.5% by volume of water and 78.5% by volume of inert gas when the top temperature of the absorption column was 62.5° C. Further, a 56 wt. % aqueous acrylic acid solution (D) was obtained from the bottom of the absorption column through line (5). It was confirmed that the yield of acrylic acid from propylene was 88%.

The process for production of acrylic acid was continued for 6 months while monitoring the amount of water by analyzing the raw gas fed to the oxidation reactor. As a result, at the days at which the temperature of outside air was below 15° C., there was observed such a tendency that the amount of water was insufficient, and, therefore, 120° C. steam was added to the circulating exhaust gas (E2) to control the water concentration of the raw gas at the inlet of the reactor to not less than 8% by volume. The compressor (18) was operated without any failure even after 6 months. As a result of overhaul and inspection after stopping the operation, it was confirmed that an inner wall surface of the mixer, etc., were free from water droplets adhered thereto.

COMPARATIVE EXAMPLE 1

The same procedure as defined in Example 1 was conducted except that the exhaust gas (E2) was heated to 80° C. by the heat exchanger (15), thereby producing acrylic acid. Although the temperature of outside air of not lower than 20° C. caused no problem, the temperature of the mixed gas was reduced to 40° C. when the temperature of outside air was decreased to 15° C. When the temperature of the mixed gas reached 36° C. owing to further decrease in temperature of outside air, the raw gas showed a tendency of reduction in water concentration thereof. Therefore, the oxidation reaction was immediately terminated to overhaul and inspect the mixer (17). As a result, it was confirmed that there were observed traces of water droplets adhered to the inner wall surface of the mixer. In addition, the compressor (18) showed traces of water droplets adhered to an inner wall surface of a suction portion thereof, and an impeller thereof also suffered from flaws that might be caused by formation of mists.

EXAMPLES 2 TO 6

The same procedure as defined in Example 1 was conducted except that production conditions were changed variously, thereby producing acrylic acid from propylene. The results are shown in Tables 1 to 3. In Example 6, the temperature of the mixed gas was controlled to 54° C. which was higher than a dew point thereof, i.e., 40° C., by heating the air to be mixed with the exhaust gas (E2). The water concentration in exhaust gas (E2) was controlled by adjusting a flow amount of absorption water and a top pressure of the absorption column. The amount of water fed to the oxidation reactor was measured by a water content meter disposed at an inlet thereof. In any of these Examples, the compressor (18) was free from problems.

TABLE 1

| | Composition at inlet of oxidation reactor | | | |
|---|---|---|---|---|
| | Propylene (vol. %) | Air (vol. %) | Water (vol. %) | Inert gas (vol. %) |
| Example 2 | 5 | 45 | 5 | 45 |
| Example 3 | 6 | 48 | 6 | 40 |
| Example 4 | 6 | 48 | 9 | 37 |
| Example 5 | 8 | 64 | 12 | 16 |
| Example 6 | 7 | 70 | 7 | 16 |

TABLE 2

| | Amount of absorbed water in absorption column (Kg/hr) | Top temperature of absorption column (° C.) | Temperature of exhaust gas (E2) (° C.) |
|---|---|---|---|
| Example 2 | 9.6 | 43 | 45 |
| Example 3 | 11.5 | 51 | 75 |
| Example 4 | 13.9 | 59 | 95 |
| Example 5 | 27 | 76 | 160 |
| Example 6 | 20 | 67 | 67 |

TABLE 3

| | Temperature of air (° C.) | Composition of mixed gas (at inlet of compressor) | | |
|---|---|---|---|---|
| | | Air (vol. %) | Water (vol. %) | Inert gas (vol. %) |
| Example 2 | 27 | 47.4 | 5.3 | 47.4 |
| Example 3 | 5 | 51.1 | 6.4 | 42.6 |
| Example 4 | 18 | 51.1 | 9.6 | 39.4 |
| Example 5 | 23 | 69.6 | 13.0 | 17.4 |
| Example 6 | 50 | 75.3 | 7.5 | 17.2 |

| | Mixed gas | |
|---|---|---|
| | Temperature (° C.) | Dew point (° C.) |
| Example 2 | 36 | 33 |
| Example 3 | 39 | 36 |
| Example 4 | 55 | 45 |
| Example 5 | 63 | 51 |
| Example 6 | 54 | 40 |

EXAMPLE 7

Exhaust gas (E2) was discharged from a top of absorption column (13) and fed through line (9) to finned tube-type heat exchanger (15) where the exhaust gas was heated to 100° C. The exhaust gas was then fed through flow control valve (16) and line (10) to a sparger provided inside of mixer (17). Simultaneously, air maintained at 15° C. was fed from a bottom of the mixer. As the mixer, there was used a mixer (17) including a tank having an inner diameter of 15.5 cm and a length of 50 cm in an upper portion of which three porous plates having apertures of 20 mm in diameter and an aperture area percentage of 25% were disposed at intervals of 10 cm. The residence time of the mixed gas from the sparger of mixer to a suction inlet of compressor (18) was 0.3 second. Also, the temperature of the gas at the suction inlet of compressor (18) was 42° C., and the dew point thereof was 40° C. Further, it was confirmed that the mixed gas had a composition that a volume ratio (%) of air: water: inert gas was 67.7:7.6:24.7.

After pressurizing the mixed gas by compressor (18), propylene was added thereto to prepare a raw gas composed of 7% by volume of propylene, 63% by volume of air, 7% by volume of water and 23% by volume of inert gas (excluding nitrogen gas contained in air mixed). 100 Nm$^3$ of the thus obtained raw gas was fed to front-stage oxidation reactor (11) and successively to rear-stage oxidation reactor (12).

The reaction gas having a temperature of 255° C., which was obtained from rear-stage oxidation reactor (12) was cooled to 160° C. by a heat exchanger and then introduced through line (4) into absorption column (13) of the same type as used in Example 1. A part of an aqueous acrylic acid solution removed from a bottom of the absorption column was cooled to 60° C. by heat exchanger (14) and circulated through line (6) to an intermediate portion of the absorption column to rapidly cool and condense the oxidation reaction gas. An aqueous solution (C) containing 200 ppm of hydroquinone was supplied from the top of absorption column (13) at a feed rate of 13.4 1/hr through line (7). When the top temperature of absorption column (13) was 63° C., the exhaust gas (E2) discharged from the top thereof was composed of 0.03% by volume of acrylic acid, 21.5% by volume of water and 78.4% by volume of inert gas.

Further, a 55 wt. % aqueous acrylic acid solution was obtained from the bottom of the absorption column through line (5). The yield of acrylic acid from propylene was 89%. It was confirmed that the compressor (18) was continuously operated without any particular problems for 6 months.

COMPARATIVE EXAMPLE 2

The same procedure as defined in Example 7 was conducted except that no mixer was used therein, thereby producing acrylic acid. More specifically, the feed conduit (10) for exhaust gas (E2) and air feed conduit (2) were directly connected to suction conduit (3) of compressor (18). The suction conduit (3) had an inner diameter of 41 mm and a length of 2.5 m, and the temperature of the gas within the suction conduit was 39° C. After 24 hours, the operation of compressor (18) was terminated to overhaul and inspect the suction conduit. As a result, it was confirmed that an inner wall surface of compressor (18) was wetted, and water droplets were adhered thereto. Although the compressor (18) was free from failure since it was operated only for a short period of time, it was expected that if the operation of compressor (18) was continued, an impeller thereof suffered from abrasion due to formation of mists.

INDUSTRIAL APPLICABILITY

In the process for producing (meth)acrylic acid according to the present invention, after separating and recovering the (meth)acrylic acid, a mixed gas composed of at least a part of exhaust gas (E2) and a molecular oxygen-containing gas is fed to a compressor at a temperature higher than a dew point thereof, and then introduced into an oxidation reactor. The process of the present invention can be continuously performed for a long period of time without damage to the compressor.

The invention of claimed is:

1. A process for producing (meth)acrolein or (meth)acrylic acid, comprising:
    feeding a raw material of the (meth)acrolein or (meth)acrylic acid, and a molecular oxygen-containing gas mixed with a diluting gas and compressed by a compressor, to an oxidation reactor to conduct a catalytic gas-phase oxidation reaction therebetween;
    feeding the obtained reaction gas to an absorption column to contact with water;
    recovering an aqueous solution of the (meth)acrolein or (meth)acrylic acid from a bottom of the absorption column, and an exhaust gas from a top of the absorption column; and
    recycling a part or whole of the thus recovered exhaust gas to use the gas as the diluting gas,
    wherein the diluting gas and the molecular oxygen-containing gas are mixed with each other using a mixer, a residence time of the mixed gas from mixing of the diluting gas with the molecular oxygen-containing gas to introduction into the compressor is not less than 0.3 second, and a temperature of a mixed gas containing the molecular oxygen-containing gas and the diluting gas at a suction inlet of the compressor is in the range of 35 to 70° C.

2. A process according to claim 1, wherein the temperature of the diluting gas upon being mixed with the molecular oxygen-containing gas is in the range of 40 to 160° C.

3. A process according to claim 2, wherein the diluting gas is heated and then mixed with the molecular oxygen-containing gas.

4. A process according to claim 3, wherein the diluting gas is heated by using a heat exchanger or by a means for mixing with steam.

5. A process according to claim 1, wherein the temperature of the molecular oxygen-containing gas upon being mixed with the diluting gas is in the range of 30 to 70° C.

6. A process according to claim 1, wherein a pressure of the mixed gas at the suction inlet of the compressor is in the range of from atmospheric pressure to a pressure lower by 10% than the atmospheric pressure.

7. A process according to claim 1, wherein the molecular oxygen-containing gas is air, and at the suction inlet of the compressor, the volume ratio (%) of air: water: the inert gas is 40 to 76:5 to 13: 10 to 50.

* * * * *